United States Patent

Hanamura et al.

[11] Patent Number: 5,621,488
[45] Date of Patent: Apr. 15, 1997

[54] APPARATUS FOR IMAGING AND DIAGNOSING A CORNEA

[75] Inventors: Yoshihiko Hanamura; Kouji Nishio; Yasufumi Fukuma, all of Tokyo, Japan

[73] Assignee: Kabushiki Kaisha TOPCON, Tokyo, Japan

[21] Appl. No.: 569,832

[22] Filed: Dec. 7, 1995

Related U.S. Application Data

[63] Continuation of Ser. No. 173,074, Dec. 27, 1993, abandoned.

[30] Foreign Application Priority Data

Dec. 28, 1992 [JP] Japan .................................. 4-348623

[51] Int. Cl.$^6$ .................................. A61B 3/14; A61B 3/10
[52] U.S. Cl. .......................... 351/206; 351/205; 396/18
[58] Field of Search .................................. 351/200, 205, 351/206, 212, 211, 214, 221; 354/62

[56] References Cited

U.S. PATENT DOCUMENTS

| | | | |
|---|---|---|---|
| 4,976,535 | 12/1990 | Reis | 351/216 X |
| 5,054,907 | 10/1991 | Sklar et al. | 351/212 |
| 5,098,426 | 3/1992 | Sklar et al. | 351/209 |
| 5,240,006 | 8/1993 | Fujii et al. | 351/221 X |
| 5,381,194 | 1/1995 | Nishio et al. | 351/208 |

*Primary Examiner*—Hung X. Dang
*Attorney, Agent, or Firm*—Finnegan, Henderson, Farabow, Garrett & Dunner, L.L.P.

[57] ABSTRACT

An apparatus for ascertaining the number of cells of an endothelium of a cornea of a subject's eye includes a display for displaying an image of cells of an endothelium of a photographed cornea, square meshes for partitioning the image of the cells displayed on the display by the unit area, and an enlarging device for enlarging and displaying an area partitioned by one of the square meshes on the display. The square meshes and the image are correlatively moved in a right or left direction on the display. An operator counts the number of the cells per unit area in an enlarged image, so that the operator ascertains the total number of the cells of the corneal endothelium.

12 Claims, 6 Drawing Sheets

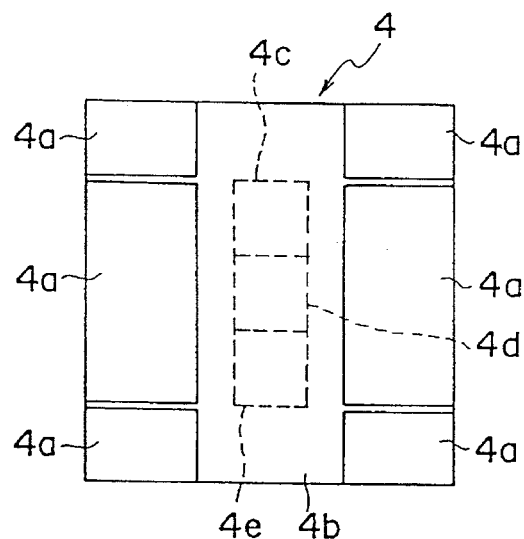
FIG. I(A)
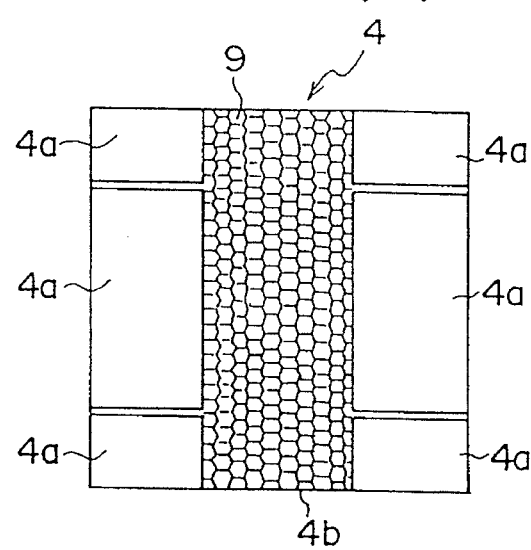
FIG. I(B)
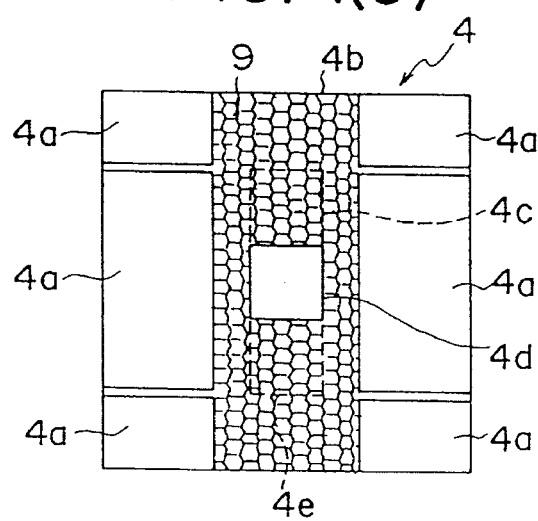
FIG. I(C)
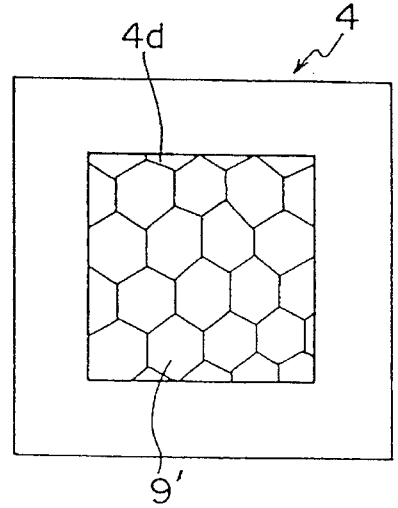
FIG. I(D)

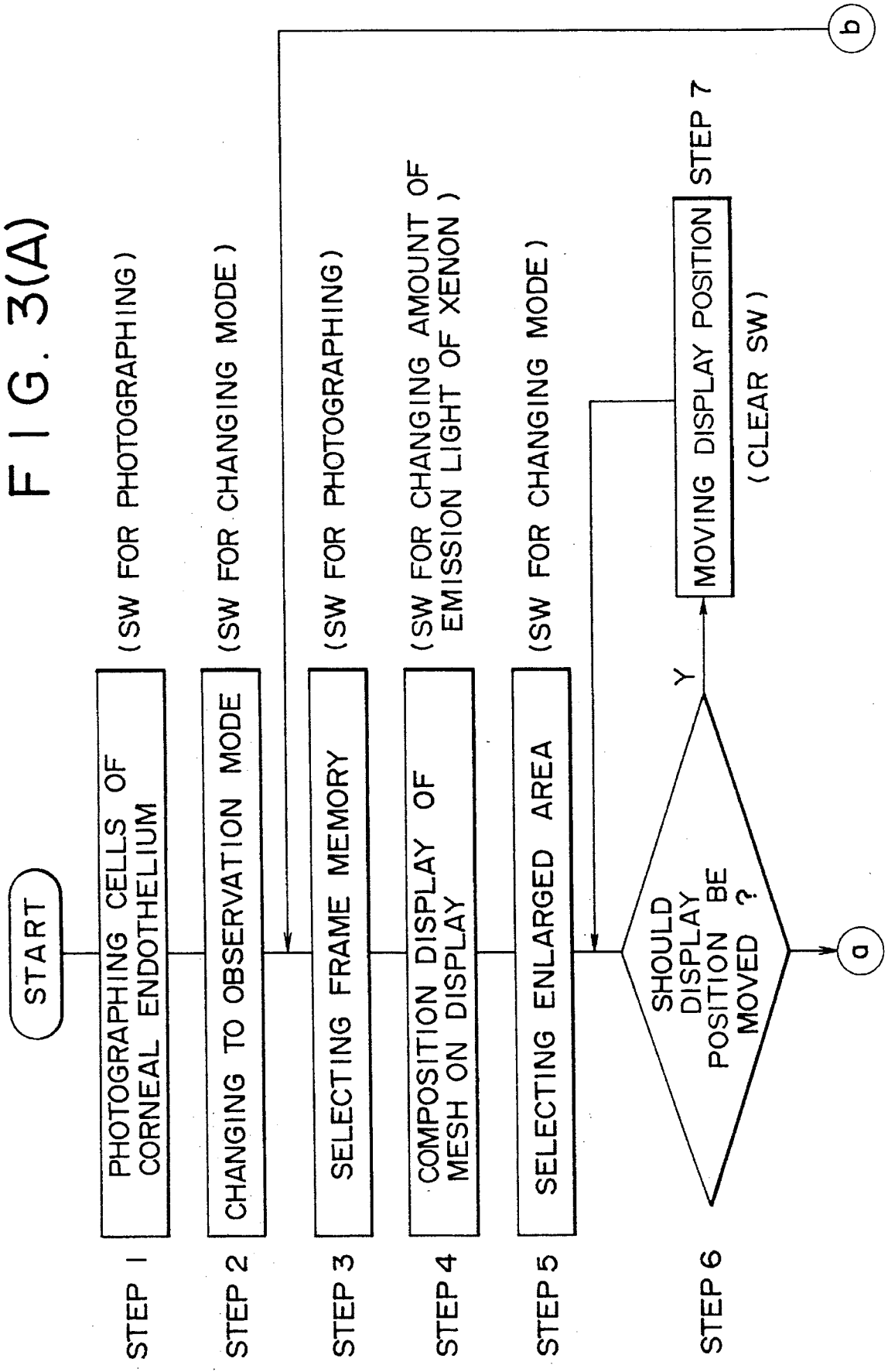

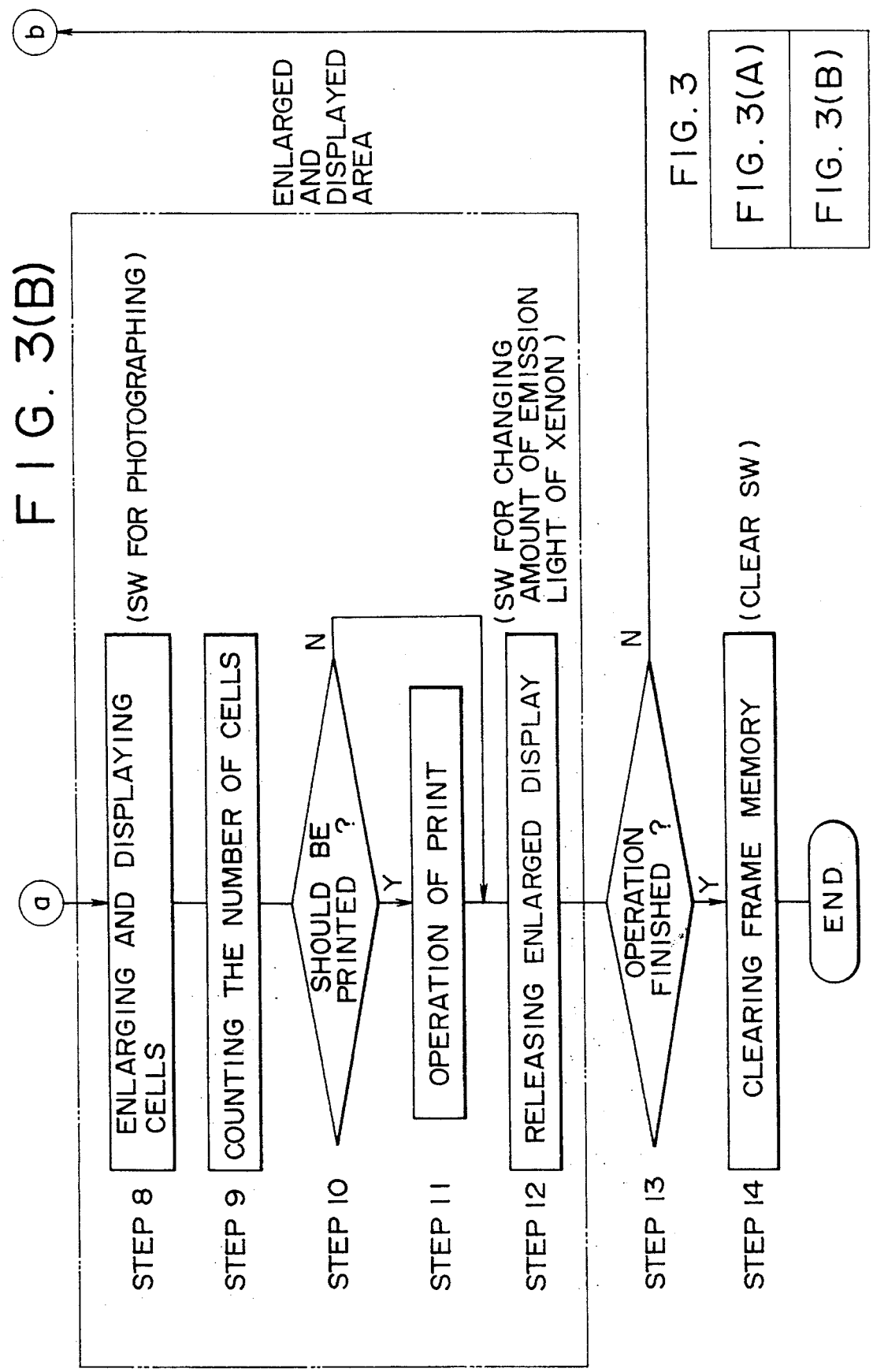

APPARATUS FOR IMAGING AND DIAGNOSING A CORNEA

This application is a continuation of application Ser. No. 08/173,074 filed Dec. 27, 1993, now abandoned.

BACKGROUND OF THE INVENTION

1. Field of the Invention

This invention relates to an ophthalmologic image processing apparatus for ascertaining the number of cells of a corneal endothelium in a photograph taken by projecting illumination light onto the cornea of a subject's eye.

2. Description of the Prior Art

In the medical field, it is said that the number of cells of a corneal endothelium ranges, as a whole, from 4,000 to 5,000 in infancy. When one of these many cells is died, the blighted cell is sucked by a cell adjacent to it. Accordingly, as we grow older, the number of the cells decreases and the corneal endothelium itself increases in size.

Further, it is said that a cornea may catch some disease, such as infection, due to no nutrition to the cornea if the number of the cells becomes below 500.

For this reason, if the number of the cells is below 500, a keratotomy is not usually performed from fear that the cells may be killed when the cornea is cut.

That is, in the field of ophthalmologic operations, an operator observes the state of the cells and counts the number of them before performing an operation on the cornea. In other words, the operator ordinarily ascertains whether a certain number of cells are still alive even if some cells are killed by the artificial cornea-cutting operation. After the operation, the operator inspects the state of the endothelium of the operated cornea at regular intervals of time.

As an apparatus for observing or photographing a corneal endothelium, a non-contact type of apparatus has been developed in which a slit lamp is provided with an optical attachment for observing a corneal endothelium.

In order to ascertain the number of the cells of the corneal endothelium, sample patterns A, B, and C which are hereinafter described are employed. For example, the sample patterns A, B, and C are each a square frame. FIGS. 4(A), 4(B), and 4(C) show the sample patterns A, B, and C, respectively. Hexagon-like cell patterns 10, 11, and 12 are represented on the sample patterns A, B, and C, respectively. The cell patterns 10, 11, and 12 are arranged to be different in size from each other because there is a correlation between the size of the cells and the number of the cells.

FIG. 4(C) corresponds to a corneal endothelium having large-sized cells the whole number of which is equal to, for example, 500. FIG. 4(B) corresponds to a corneal endothelium having medium-sized cells the whole number of which is equal to 1,000. FIG. 4(A) corresponds to a corneal endothelium having small-sized cells the whole number of which is equal to 1,500.

After photographing the corneal endothelium, the operator compares the size of the cells appearing in a photograph with the size of the cell patterns represented on the sample patterns, thereby judging that the photographed cells correspond to any of the cell patterns of the sample patterns A, B, and C, so that the operator ascertains the number of the cells.

For example, if the size of the photographed cells corresponds to the size of the cell pattern 11 represented on the sample pattern B, the operator presumes that the number of the cells is equal to 1,000. Likewise, if the size of the photographed cells corresponds to the medium between the size of the cell pattern 11 of the sample pattern B and the size of the cell pattern 12 of the sample pattern C, the operator presumes that the number of the cells is equal to about 750.

According to a method in which the size of the cells of the corneal endothelium is decided by using the sample patterns A, B, and C to ascertain the number of the cells, it is not required to employ a circuit for calculating the number of the cells or an expensive image analysis apparatus.

However, since an coincidence is not always brought about between the size of the photographed cells and the size of the cell patterns of the sample patterns, it is difficult to correctly count the total number of the cells of the corneal endothelium.

SUMMARY OF THE INVENTION

It is therefore an object of the invention to provide an ophthalmologic image processing apparatus for photographing the cells of the corneal endothelium of a subject's eye and for ascertaining the number of the cells easily and accurately.

To accomplish the object, the ophthalmologic image processing apparatus according to the invention includes a display for displaying an image of the cells of a corneal endothelium, a means for partitioning a displayed image of the cells by a unit area, and a means for enlarging and displaying a partitioned portion of the image on the display.

According to the invention, the cells of the corneal endothelium are displayed, an image of the displayed cells is partitioned by the partitioning means by a predetermined unit area, a partitioned portion of the image is moved and enlarged on the display, and the operator counts the number of the cells per unit area from the enlarged image.

Therefore, the number of the cells per unit area is counted easily and accurately. The operator obtains the total number of the cells from the number of the cells per unit area. Accordingly, the operator can precisely ascertain the number of the actual cells of the corneal endothelium.

BRIEF DESCRIPTION OF THE DRAWINGS

FIG. 1(A) to 1(E) show the state of the cells of a corneal endothelium of a subject's eye displayed at intervals of time on a display of an apparatus for ascertaining the number of the cells according to the invention, in which FIG. 1(A) shows the display where the cells are not yet displayed;

FIG. 1(B) shows the display where the cells are displayed;

FIG. 1(C) shows the display where meshes are superimposed upon the cells;

FIG. 1(D) shows the display where a portion of the cells is enlarged; and

FIG. 1(E) is a descriptive drawing showing a variant.

FIG. 3 shows how the two parts, FIG. 3(A) and FIG. 3(B), should be combined to form FIG. 3, and is a flowchart showing the effect of the apparatus according to the invention.

DESCRIPTION OF THE PREFERRED EMBODIMENT

The embodiment of an apparatus for ascertaining the number of the cells of the corneal endothelium of a subject's eye according to the invention will be hereinafter described with reference to FIGS. 1(A) to 1(E), FIG. 2, and FIG. 3.

Figure 2:
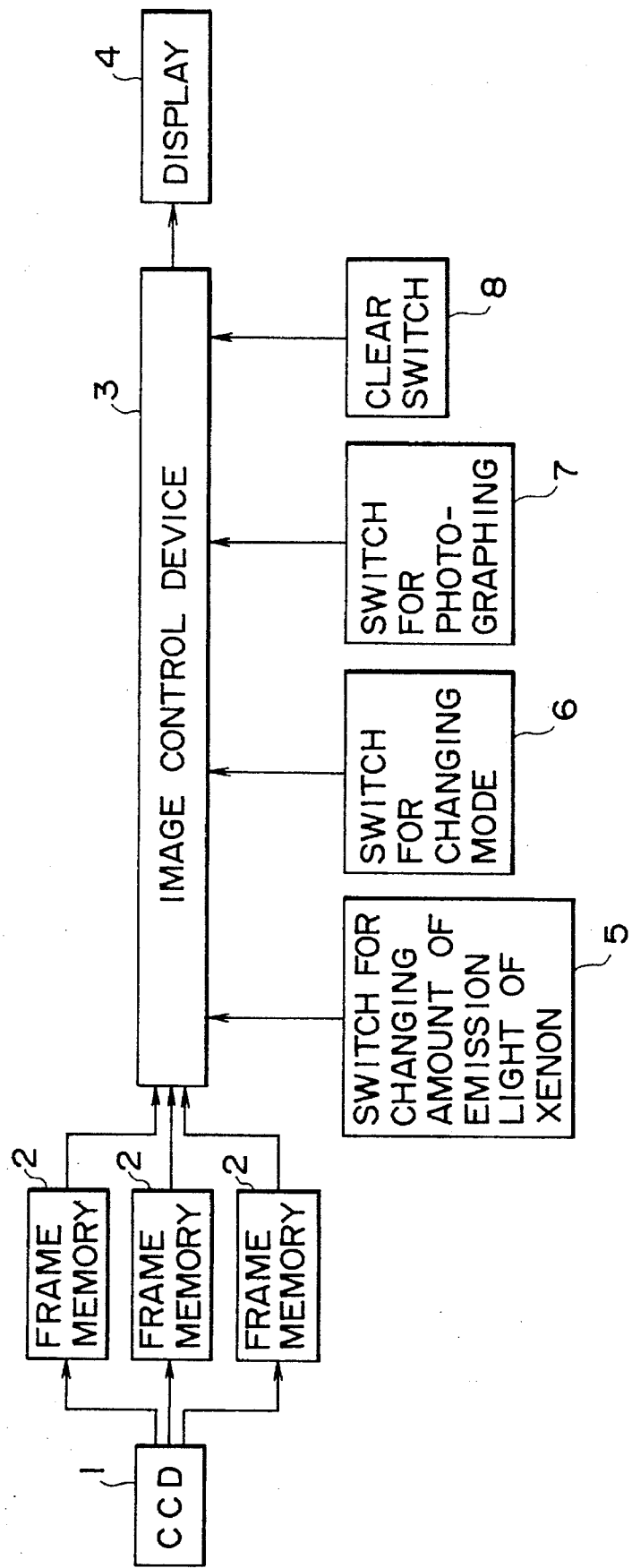
FIG. 2 is a block diagram showing a main part of the apparatus according to the invention.
Figure 4A:
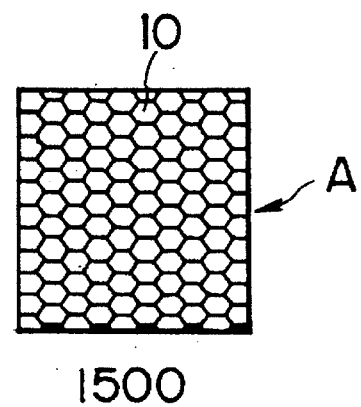
FIGS. 4(A) to 4(C) show sample patterns for describing the prior art.
Figure 4B:
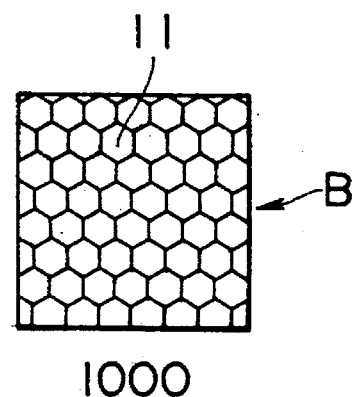
Figure 4C:
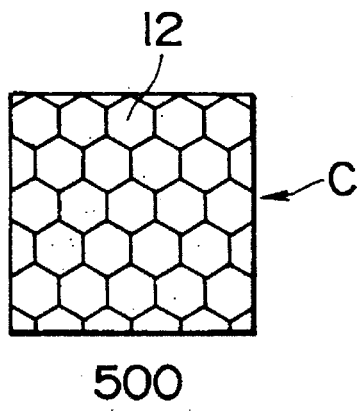

Referring to FIG. 2, the numerals 1 and 2 indicate a charge coupled device (CCD) and a frame memory, respectively. The CCD 1 receives an image reflected from a cornea through an observation optical system (not shown). The cornea is illuminated with slit light of an illumination optical system. Light reflected by the cornea is received by the observation optical system. The number of the frame memories 2 is equal to three in this embodiment.

The image of the cells of the corneal endothelium received by the CUD 1 is temporarily stored in a first frame memory 2 at the same time when the cells are photographed. An image control device 3 causes the image stored in the first frame memory 2 to be displayed on a display 4. While the cells are observed, the image control device 3 causes the stored image to be displayed in real time. The image control device 3 includes a switch 5 for chansing the amount of emission light of xenon from a high level to a low level and vice versa when photographed, a switch 6 for changing a mode from a photographing mode to an observation mode and vice versa, a switch 7 for photographing, and a clear switch 8 for deleting images stored in the frame memories 2. The display 4 is controlled by these switches.

FIG. 1(A) shows the initial state of the display 4. The reference numeral 4a indicates an area corresponding to a mask of the observation optical system (not shown). The reference numeral 4b indicates an area for displaying an image 9 of the cells of the corneal endothelium. The reference numerals 4c, 4d, and 4e indicate areas where three square meshes (partitioning means) are each located. The meshes 4c to 4e are shown by stitch lines.

As shown in FIG. 1(B), the image 9 of the cells is displayed in the area 4b.

The image 9 to be displayed in the area 4b is an image of the cells received by the CCD 1 or an image of the cells stored in the frame memory 2. The meshes 4c, 4d, and 4e are each a square frame the size of which is, for example, 0.1 mm×0.1 mm. These meshes 4c, 4d, and 4e can be displayed by magnifying the 0.1 mm×0.1 mm-sized frame at the same magnification as the image 9.

Further, one of the meshes 4c, 4d, and 4e is selected and magnified to be displayed on the display 4. FIG. 1(D) shows such a magnified frame 4d together with a magnified image 9' of the cells.

The operator can obtain the number of the cells per unit area by counting the number of the magnified cells 9'. Thereby, the total number of the cells 9 of the corneal endothelium can be ascertained. As described hereinafter, the functions of the switches 5, 7, and 8 are each changed by the mode selecting switch 6.

With reference to the flowchart shown in FIG. 3, a description will now be given of the steps of observing or photographing the cells of the corneal endothelium by means of the apparatus for observing or photographing the cells and of ascertaining the number of the cells from its resultant image.

(Step 1)

When the photographing switch 7 is turned on, the cornea is illuminated with slit light of the illumination optical system (not shown). An image reflected by the cornea is guided through the observation optical system to the CCD 1 by which the cells of the corneal endothelium are photographed. The image of the cells received by the CCD 1 is stored in the frame memory 2. When the photographing which is repeated desired times is completed, the step shifts from Step 1 to Step 2. In this embodiment, the photographing can be carried out at most three times at a time because the number of the frame memories 2 is equal to three. The operator causes the images of the cells stored in the frame memories 2 to be displayed on the display 4, thereby selecting an image which is in clear focus from them.

(Step 2)

Let it be supposed that the cells are displayed in real time. When the mode selecting switch 6 is operated, an image 9 of the cells stored in the frame memories 2 is displayed in the area 4b of the display 4 as a still image (see FIG. 1(B)). This still image 9 is an image of the cells photographed at the end time. The step shifts from Step 2 to Step 3.

(Step 3)

The operator operates the photographing switch 7 to successively display the images of the cells stored in the frame memories 2 in the area 4b. From the images, the operator selects an image best in focus and causes the best image to be displayed in the area 4b. When the selection is completed, the step shifts from Step 3 to Step 4.

(Step 4)

As shown in FIG. 1(C), by operating the switch 5 for changing the amount of emission light of xenon, the image 9 of the cells is superimposed upon the meshes 4c, 4d, and 4e.

(Step 5)

By operating the mode selecting switch 6, the operator determines a portion of the image 9 for counting the number of the cells. That is, by operating the mode selecting switch 6, one of the meshes 4c, 4d, and 4e is selected. If the mesh 4d is selected as shown in FIG. 1(C), the mesh 4d is displayed differently from the other meshes 4c and 4e.

When the selection of one of the meshes 4c, 4d, and 4e is completed, the step shifts from Step 5 to Step 6.

(Step 6)

The operator judges whether the meshes 4c, 4d, and 4e or the image 9 of the cells should be moved in a right or left direction along the display 4. In other words, the operator adjusts a positional relationship between the meshes 4c–4e and the image 9 in a right or left direction. The reason for it is that the image 9 of the cells may become out of focus little by little in the right and left directions. Further, the reason is that the brightness of the image 9 is different in the right and left directions. By moving the meshes 4c–4e or the image 9 in the right or left direction, a portion of the image 9 where the number of the cells is quickly counted is fixed.

If such adjustments are required, the step shifts from Step 6 to Step 7. If not so, the step shifts from Step 6 to Step 8.

(Step 7)

The clear switch 8 is used for moving the meshes 4c–4e or the image 9 in the right or left direction. By operating the clear switch 8, the meshes 4c–4e or the image 9 is moved in the right or left direction, so that the portion of the image 9 of the cells to be counted is located in the middle of the area 4b.

(Step 8)

By operating the photographing switch 7, the selected mesh 4d and the image 9 enclosed by the mesh 4d are enlarged and displayed on the display 4 as shown in FIG. 1(D).

(Step 9)

The operator counts the number of the cells appearing in an enlarged image 9', thereby fixing the number of the cells per unit area and obtains the total number of the cells of the image 9.

(Step 10)

The operator judges whether the enlarged image 9' should be printed. If printed, the step shifts from Step 10 to Step 11. If not so, the step shifts from Step 10 to Step 12.

(Step 11)

By operating a printing switch (not shown), the enlarged image 9' is printed. The step shifts from Step 11 to Step 12. If the image 9, not enlarged, of the cells is printed, the printing switch is operated before shifting to Step 4.

(Step 12)

In order to return from the enlarged image 9' shown in FIG. 1(D) to the normal-sized image 9 shown in FIG. 1(B), the switch 5 for changing the amount of emission light of xenon is used. By operating the switch 5, the normal-sized image 9 as a still image is again displayed in the area 4b.

(Step 13)

The operator judges whether all the operations should be completed. If completed, the step shifts from Step 13 to Step 14. If the operations are repeated, the step is returned to Step 3.

That is, if the operator intends to cause the images of the cells stored in the other frame memories to be displayed on the display 4 for ascertaining the number of the cells or to change the place of the cells to be counted to another, the operations from Step 3 to Step 14 are repeated.

(Step 14)

By operating the clear switch 8, all the images of the cells stored in the frame memories 2 are deleted. All the operations for ascertaining the number of the cells are completed.

The number of the meshes is not limited to the above embodiment in which the three meshes 4c, 4d, and 4e are simultaneously displayed in the area 4b.

Figure 1E:
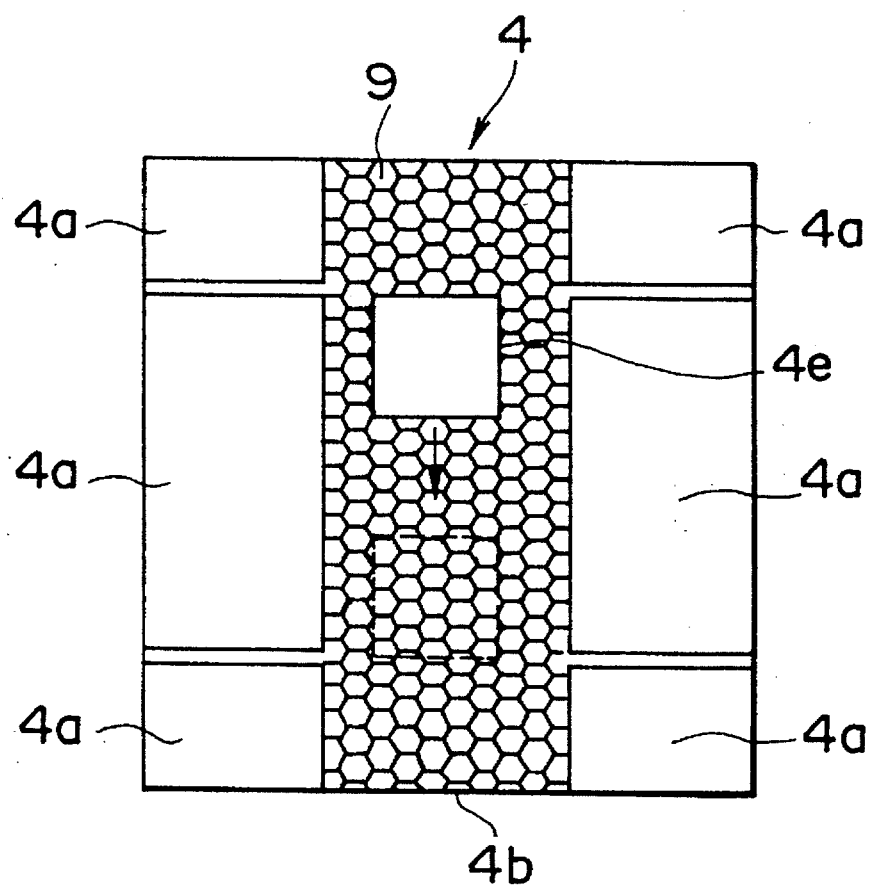

For example, as shown in FIG. 1(e), a mesh 4e may be successively moved from a position shown by the continuous line to another position shown by the phantom line.

What is claimed is:

1. An apparatus for ascertaining the number of cells of an endothelium of a cornea of a subject's eye, comprising:

means for storing an image of cells of an endothelium of a photographed cornea;

a display for displaying said stored image;

means for partitioning said image displayed on said display by a square, the square representing a unit area; and means for enlarging the square as well as the partitioned image within the enlarged square and displaying the enlarged image on said display;

wherein the number of cells in the square is the same before and after enlargement of the image.

2. The apparatus according to claim 1, wherein said partitioning means comprises a plurality of squares placed contiguously in a vertical direction on said display.

3. The apparatus according to claim 1, wherein said partitioning means comprises a square movable in a vertical direction on said display.

4. The apparatus according to claim 1, wherein said partitioning means and said image are movable in a right or left direction with respect to each other on said display.

5. An apparatus for ascertaining the number of cells of an endothelium of a cornea of a subject's eye, comprising:

means for storing an image of cells of an endothelium of a photographed cornea;

a display for displaying said stored image;

means for superimposing a square frame meaning of unit area upon said display in order to partition said cells displayed on said display by a predetermined unit area; and means for enlarging and displaying the square frame and said cells enclosed by said square on said display, wherein the number of cells in the square frame is the same before and after enlargement of the square frame.

6. The apparatus according to claim 5, wherein a plurality of square frames for partitioning said cells are displayed on said display.

7. The apparatus according to claim 6, wherein one of said square frames is selected to count the number of said cells per unit area.

8. The apparatus according to claim 6, wherein one of said square frames is selected and moved with respect to said image of said cells on said display.

9. An apparatus for ascertaining the number of cells of an endothelium of a cornea of a subject's eye, comprising:

means for storing an image of cells of an endothelium of a photographed cornea;

a display for displaying said stored image;

means for partitioning said image displayed on said display by a frame, the frame representing a unit area;

means for adjusting the frame on the displayed image in correlation with said cells; and means for enlarging the frame as well as the partitioned image within the enlarged frame and displaying the enlarged frame and image on said display, wherein the number of cells in the frame is the same before and after enlargement of the frame.

10. An apparatus for ascertaining the number of cells of an endothelium of a cornea of a subject's eye, comprising:

means for storing an image of cells of an endothelium of a photographed cornea;

a display for displaying said stored image;

means for superimposing a plurality of square frames upon said display in order to partition said cells displayed on said display by a predetermined unit area, each of said plurality of square frames being of unit area; and means for enlarging and displaying the plurality of square frames and said cells enclosed by said plurality of square frames on said display.

11. The apparatus according to claim 10, wherein one of the plurality of square frames is selected to count the number of cells per unit area.

12. The apparatus according to claim 10, wherein one of the plurality of square frames is selected and moved with respect to the image of the cells on the display.

* * * * *